United States Patent
Seavey

(10) Patent No.: US 11,199,592 B2
(45) Date of Patent: Dec. 14, 2021

(54) ROBOTIC MAGNETIC FLUX LEAKAGE INSPECTION SYSTEM FOR EXTERNAL POST-TENSIONED TENDONS OF SEGMENTAL BRIDGES AND ROADWAYS

(71) Applicant: INFRASTRUCTURE PRESERVATION CORPORATION, Clearwater, FL (US)

(72) Inventor: William Seavey, Clearwater, FL (US)

(73) Assignee: INFRASTRUCTURE PRESERVATION CORPORATION, Clearwater, FL (US)

( * ) Notice: Subject to any disclaimer, the term of this patent is extended or adjusted under 35 U.S.C. 154(b) by 173 days.

(21) Appl. No.: 15/984,804

(22) Filed: May 21, 2018

(65) Prior Publication Data

US 2018/0335482 A1 Nov. 22, 2018

Related U.S. Application Data

(60) Provisional application No. 62/508,791, filed on May 19, 2017.

(51) Int. Cl.
*G01R 33/00* (2006.01)
*H01F 27/34* (2006.01)
(Continued)

(52) U.S. Cl.
CPC ...... *G01R 33/0011* (2013.01); *A61B 17/3478* (2013.01); *G01R 33/0017* (2013.01);
(Continued)

(58) Field of Classification Search
CPC ................ G01R 33/00; G01R 33/0011; G01R 33/0017; H01F 27/34; H01F 27/346;
(Continued)

(56) References Cited

U.S. PATENT DOCUMENTS

| 4,468,619 A | 8/1984 | Reeves |
| 4,659,991 A | 4/1987 | Weischedel |

(Continued)

FOREIGN PATENT DOCUMENTS

| EP | 0266103 | 5/1994 |
| EP | 2450700 | 5/2012 |
| WO | WO2011058369 | 5/2011 |

*Primary Examiner* — Huy Q Phan
*Assistant Examiner* — David B Frederiksen
(74) *Attorney, Agent, or Firm* — Matthew G. Mckinney, Esq.; Allen, Dyer et al.

(57) ABSTRACT

A robotic inspection system for corrosion detection within external post-tension bridge tendons includes a sensing device. The sensing device is configured to move along a bridge tendon to detect magnetic flux leakage of the bridge tendon as the sensing device moves along the bridge tendon. In addition, the system includes a location device coupled to the sensing device, where the location device is configured to determine the location of the sensing device on the bridge tendon. The system also includes a control station configured to wirelessly interface with the sensing device and the location instrument. The control station is also configured to generate a bridge tendon condition assessment report from the detection of magnetic flux leakage to identify locations and sizes of discontinuities of the bridge tendon.

14 Claims, 5 Drawing Sheets

(51) Int. Cl.
  *A61B 17/34* (2006.01)
  *A61B 17/00* (2006.01)
  *A61M 5/19* (2006.01)

(52) U.S. Cl.
  CPC .... *H01F 27/346* (2013.01); *A61B 2017/0034* (2013.01); *A61B 2017/00269* (2013.01); *A61B 2017/00942* (2013.01); *A61M 5/19* (2013.01)

(58) Field of Classification Search
  CPC ...... G01N 27/20; G01N 27/226; G01N 27/24; G01N 27/82–9093
  See application file for complete search history.

(56) References Cited

U.S. PATENT DOCUMENTS

| | | | | |
|---|---|---|---|---|
| 5,321,356 | A * | 6/1994 | Weischedel | G01N 27/82 324/240 |
| 5,581,037 | A | 12/1996 | Kwun et al. | |
| 5,821,749 | A * | 10/1998 | Booker | G01N 27/9013 324/240 |
| 6,633,159 | B1 | 10/2003 | Robar et al. | |
| 6,967,478 | B2 * | 11/2005 | Wayman | G01N 27/82 324/235 |
| 8,844,387 | B1 * | 9/2014 | Tunacik, Jr. | G01M 5/0058 73/159 |
| 9,470,657 | B2 * | 10/2016 | Ouellette | G01B 7/046 |
| 9,535,026 | B2 | 1/2017 | Marashdeh et al. | |
| 9,828,216 | B2 * | 11/2017 | Berben | B66B 7/1223 |
| 2004/0016299 | A1 * | 1/2004 | Glascock | G01N 29/221 73/638 |
| 2010/0052670 | A1 * | 3/2010 | Kwun | G01N 29/2412 324/240 |
| 2010/0148766 | A1 * | 6/2010 | Weischedel | G01N 27/9006 324/238 |
| 2011/0006762 | A1 * | 1/2011 | Yoshioka | G01N 27/83 324/240 |
| 2011/0068773 | A1 * | 3/2011 | Harkness | G01R 15/186 324/127 |
| 2014/0035569 | A1 * | 2/2014 | Yoshioka | G01N 27/82 324/242 |
| 2014/0116715 | A1 * | 5/2014 | Sipila | E21B 47/06 166/336 |
| 2014/0368191 | A1 * | 12/2014 | Goroshevskiy | G01N 27/85 324/201 |
| 2015/0130454 | A1 * | 5/2015 | Itoi | G01N 27/82 324/240 |
| 2016/0025680 | A1 | 1/2016 | Schein, Jr. | |
| 2017/0023531 | A1 * | 1/2017 | Vinogradov | G01N 29/2412 |
| 2018/0117976 | A1 * | 5/2018 | Gramling | G01N 27/82 |

* cited by examiner

ROBOTIC MAGNETIC FLUX LEAKAGE INSPECTION SYSTEM FOR EXTERNAL POST-TENSIONED TENDONS OF SEGMENTAL BRIDGES AND ROADWAYS

RELATED APPLICATION

The present invention is related to U.S. Provisional Patent Application Ser. No. 62/508,791 filed May 19, 2017, the entire contents of which are incorporated herein by reference.

TECHNICAL FIELD

The present invention relates to the field of bridge inspection devices, and, more particularly, to a robotic magnetic flux leakage inspection system for external post-tensioned tendons of segmental bridges and roadways.

BACKGROUND

The corrosion of post-tensioned bridge tendons is a serious problem that can compromise the structural integrity of a bridge with minimal visual signs. Consequently, the early detection of deficiencies of the bridge tendons is a major safety issue. Without detection, steel corrosion can occur to the point of collapse without any major outward visual signs.

Methods of locating deficiencies within the tendon ducts can be categorized as either destructive or nondestructive. Destructive test methods require some degree of repair after the testing has been completed. By contrast, nondestructive test methods do not require repair after the testing has been completed. However, existing nondestructive test methods are not able to inspect bridge tendons where there is minimal or no clearance around the bridge tendon for the inspection. In addition, the type of inspections that can be performed using nondestructive devices has been limited.

It is, therefore, to the effective resolution of the aforementioned problems and shortcomings of the prior art that the present invention is directed.

However, in view of the prior art at the time the present invention was made, it was not obvious to those of ordinary skill in the pertinent art how the identified needs could be fulfilled.

SUMMARY

In a particular embodiment, a robotic inspection system to detect discontinuities within external post-tension bridge tendons is disclosed. The system includes a sensing device configured to move along an outer surface of a bridge tendon to detect magnetic flux leakage within the bridge tendon, and a location device is coupled to the sensing device and configured to determine the location of the sensing device on the bridge tendon. In addition, the system includes a control station configured to wirelessly interface with the sensing device and the location device, where the control station is configured to generate a bridge tendon condition assessment report from the detection of the magnetic flux leakage to identify locations and sizes of the discontinuities within the bridge tendon.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The robotic inspection system utilizes a non-destructive testing (NDT) method to locate and assess the condition of external post-tensioned tendons of segmental bridges and roadways. In particular, cross-sectional damage can occur in steel cables within the bridge tendons due to corrosion and fracture, which can lead to stress concentrations. Cross-sectional damage can be a direct cause of structural failure. Therefore, nondestructive evaluation (NDE) is necessary to detect the initial stages of cross sectional damage in a cable. However, it is difficult to monitor the condition of most cables, as the damage can be invisible and inaccessibly located. Accordingly, the present invention utilizes a magnetic flux leakage (MFL) method to detect discontinuities.

The MFL method includes magnetizing the bridge tendon and the cables housed therein. The bridge tendon that is magnetized has a magnetic field in and around itself. The magnetic field spreads out when it encounters a small air gap created by a discontinuity and it appears to leak out of the bridge tendon. A strong permanent magnet or an electromagnet is used to establish a magnetic flux in the bridge tendon to be inspected. When there is no defect, the flux in the metal remains uniform. However, when there is a discontinuity the flux leaks out of the metal near the discontinuity. A sensor array is configured to detect this flux leakage and to generate an electric signal that is proportional to the magnetic flux leakage.

Referring now to FIGS. 1-4, the robotic system includes a sensing device 100, which may be a wireless and battery operated mobile transport. In a particular embodiment, the sensing device 100 is coupled completely around (360 degrees) a bridge tendon 110 and travels along the bridge tendon 110 performing an inspection of the condition of the steel cables within the bridge tendon 110.

Figure 1:
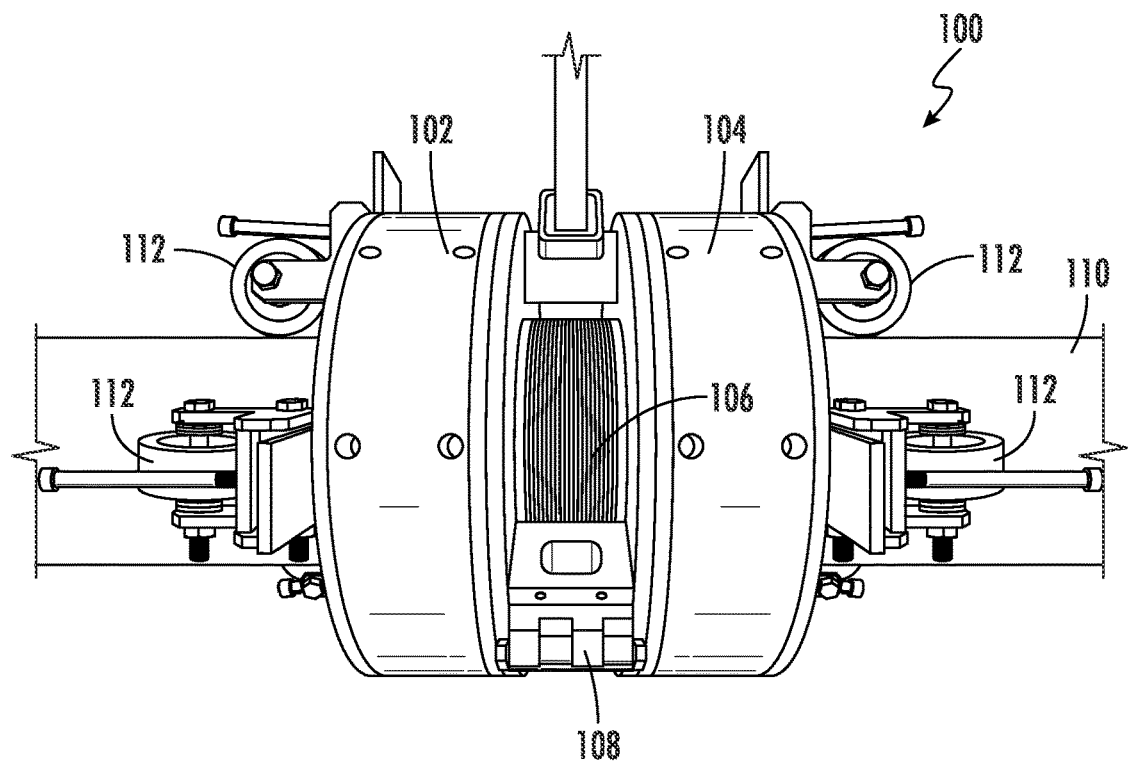
FIG. 1 is a elevational side view of a first embodiment of a sensing device of the present invention secured around a tendon.

A first embodiment of the sensing device 100 is shown in FIG. 1 secured around the bridge tendon 112 and performing an inspection. The sensing device 100 may be self-propelled, and operate on battery power with wireless connectivity to a control station. Alternatively, the sensing device 100 can be rolled along the bridge tendon 110 by the inspector. The inspections are real-time with minimum back office processing.

Figure 9:
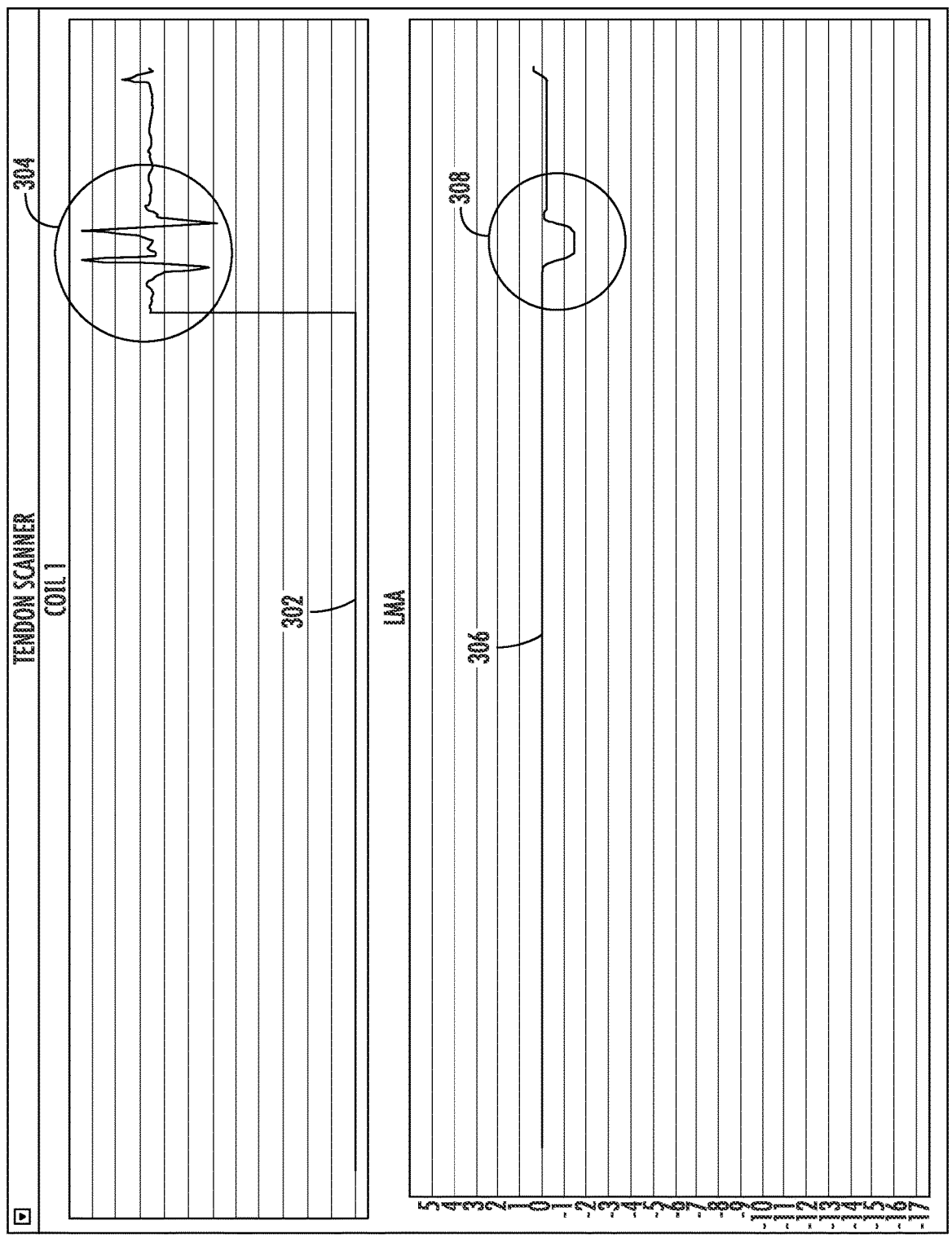
FIG. 9 is an exemplary graph generated by the sensing device.

In a particular illustrative embodiment, the sensing device 110 uses the magnetic flux leakage (MFL) method described above to generate a visual indicator of the condition of the bridge tendon 110. For example, the visual indicator may be a two dimensional graph (as shown in FIG. 9 discussed below) that indicates where the discontinuity within the bridge tendon 112 is located and to what degree. The sensing device 100 takes multiple measurements of the magnetic field at the periphery of the bridge tendon 110 and combines these measurements to provide information of the magnetic properties of the process volume to indicate the extent of loss of magnetic area. This correlates to the amount of steel within the bridge tendon 100 that may be damaged.

Figure 2:
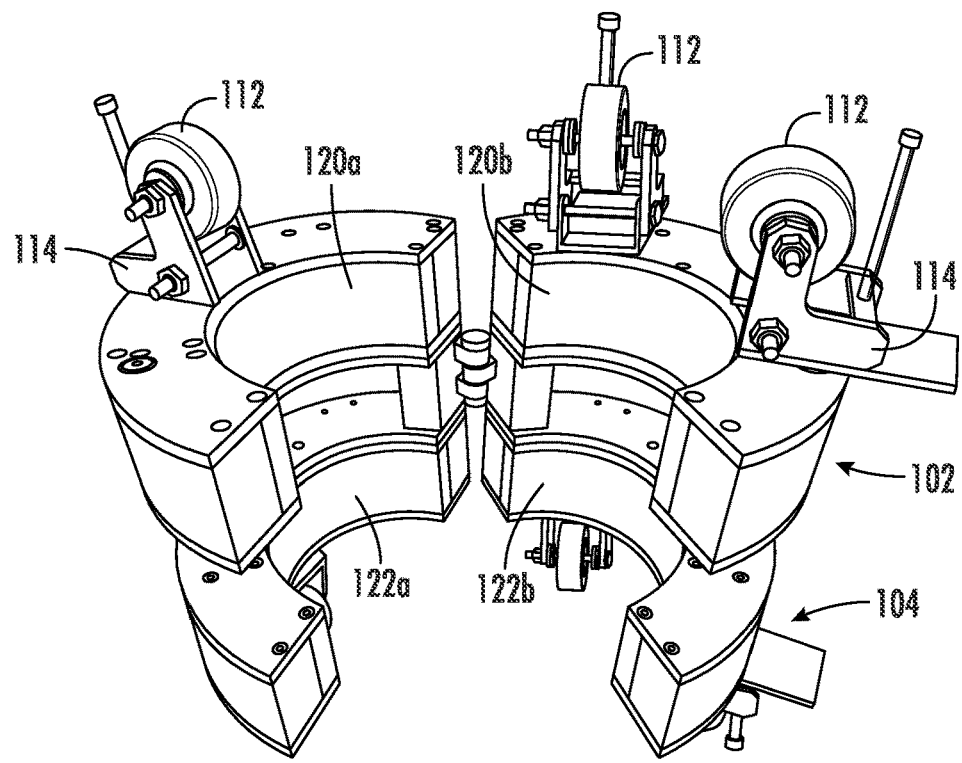
FIG. 2 is a top perspective view of the sensing device in an open position.

The sensing device 100 includes a first magnet 102 having a first polarity and a second magnet 104 having a second polarity. The first and second magnets 102, 104 may comprise sets of rare-earth magnets grouped in measurement channels, where each of which delivers a cross-sectional magnetic field. The sensing device 100 also includes a sensor array 106 that has a curved or arcuate shape as shown in FIGS. 1 and 2 and may be coupled to a processor that is configured to analyze raw voltage measurements from the sensor array 106 using algorithms and provide analysis and export of graphical data. The sensor array 106 is configured to detect the magnetic flux leakage perpendicular to a surface of the bridge tendon 110. The sensor array 106 comprises an inductive coil sensor or Hall effect sensor configured to detect the magnetic flux leakage to indicate a discontinuity within the bridge tendon 110.

Figure 4:
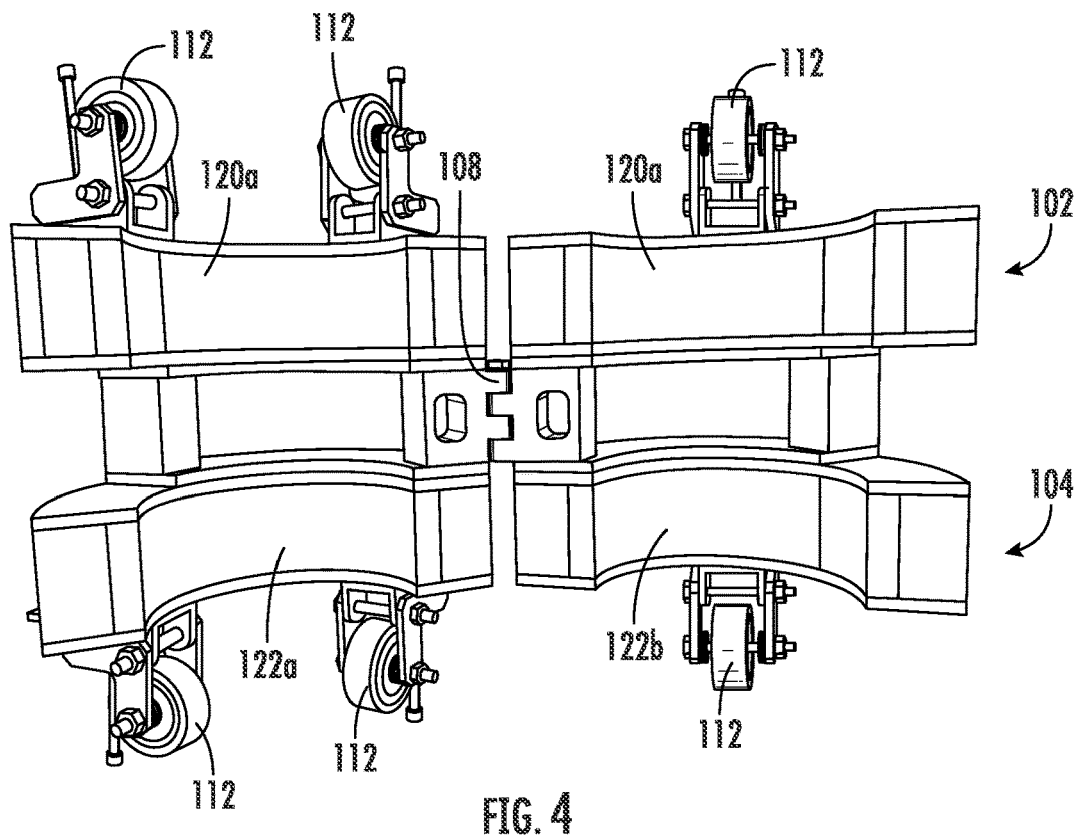
FIG. 4 is an elevational side view of the sensing device in an open position.
Figure 5:
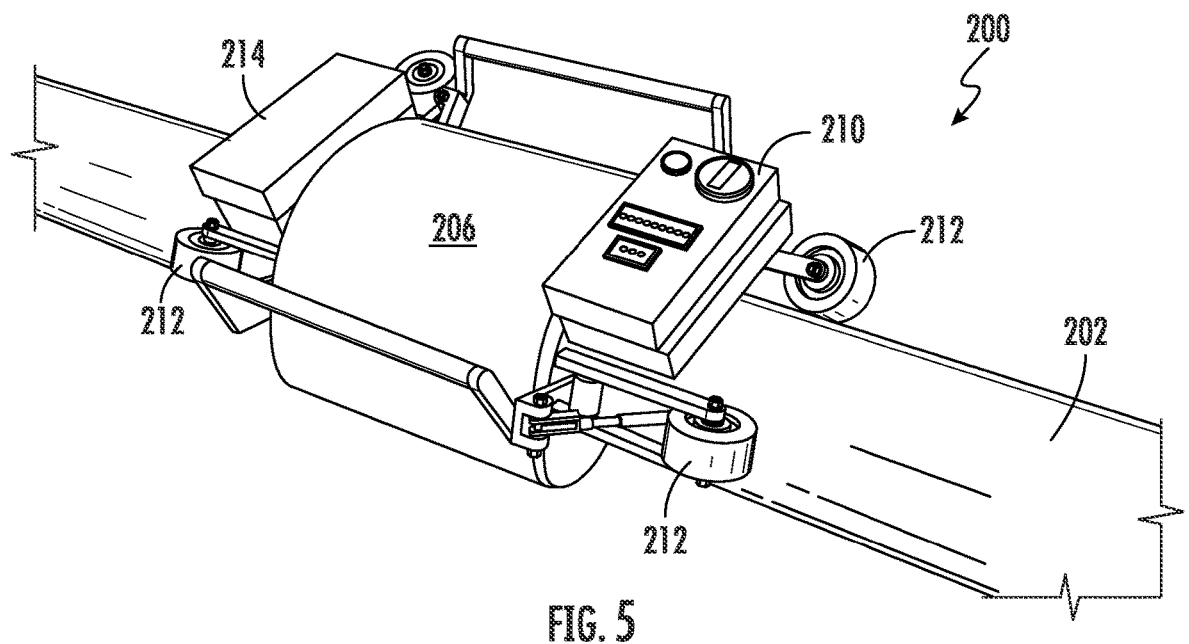
FIG. 5 is a perspective view of a second embodiment of the sensing device secured around a tendon.

As shown in FIGS. 2 and 4, the first magnet 102 has a curved or arcuate shape and comprises two halves 120a, 120b, that are hingedly coupled to each other by clasp 108. Similarly, the second magnet 104 has a curved or arcuate shape and comprises two halves 122a, 122b that are hingedly coupled to each other by clasp 108. Accordingly, the first and second arcuate magnets 102, 104 can be swung apart so that the sensing device can be secured completely around the bridge tendon 110.

Figure 3:
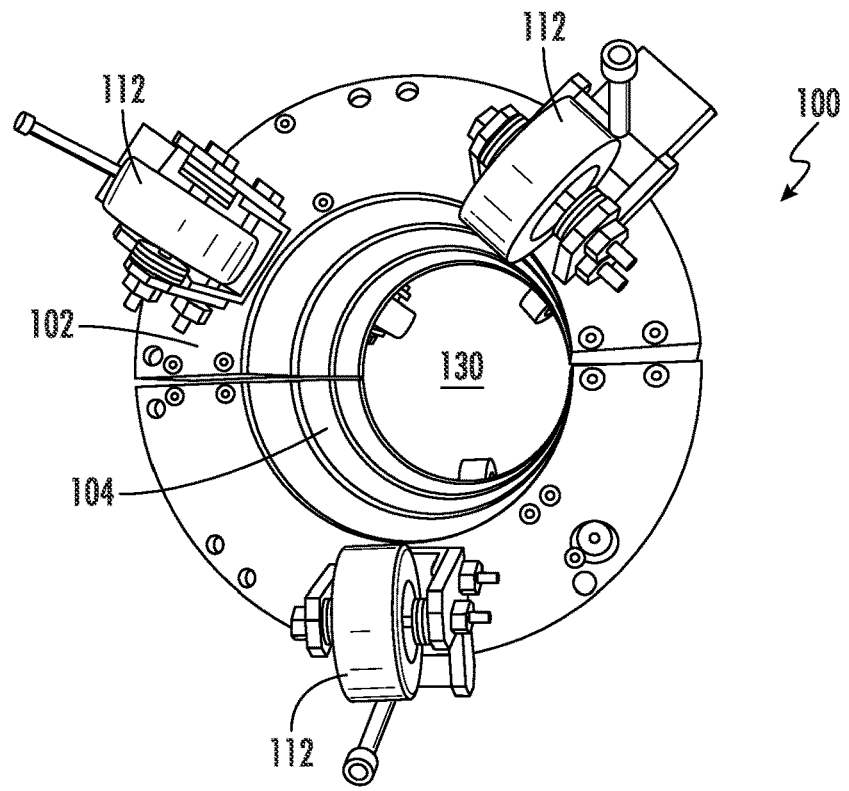
FIG. 3 is a top perspective view of the sensing device in a closed position.

Once the sensing device 100 is secured to the bridge tendon 110 creating a center aperture 130 as shown in FIG. 3, the wheels 112 can be adjusted using respective wheel clamps 114 so that the first and second magnets 102, 104 can be rolled along the bridge tendon 110 passing adjacent within a few inches of the exterior surface of the bridge tendon 110.

Figure 6:
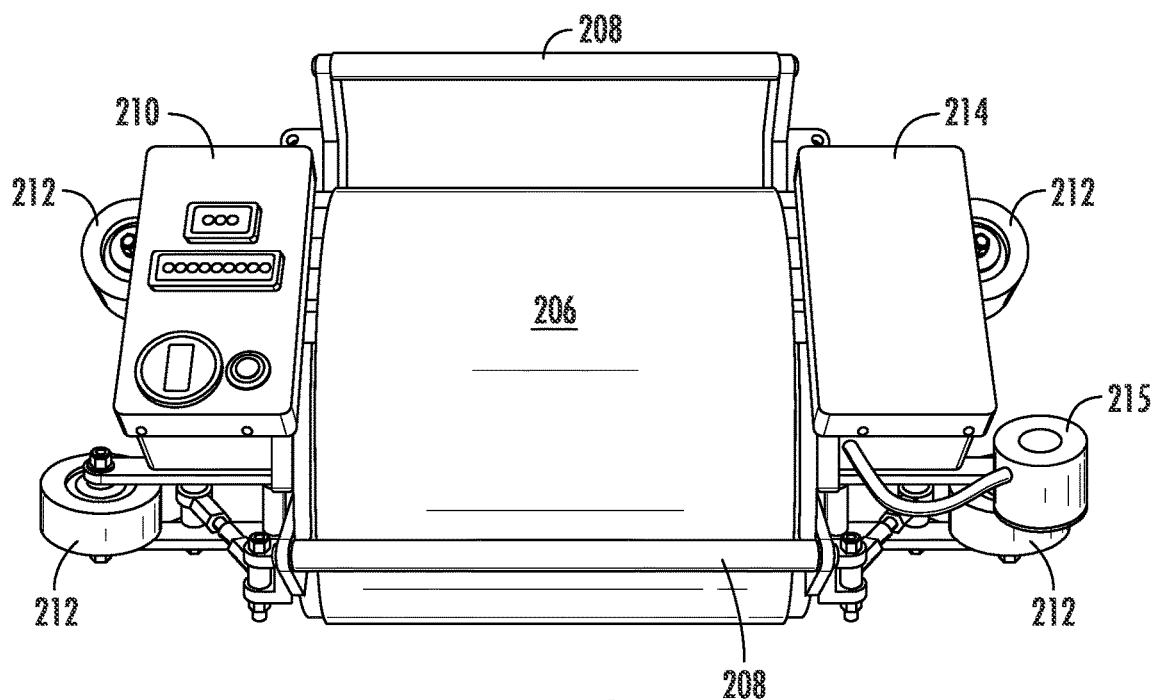
FIG. 6 is an elevational side view of a closed side of the sensing device.

The second embodiment of the sensing device 200 is shown in FIGS. 5-8. In contrast to the first embodiment described above, the sensing device 200 is configured to surround about 240 degrees around the bridge tendon 202 (with 360 degrees being completely around). As shown in FIG. 6, the sensing device 200 includes a housing 206 and grab rails 208 that can be used by the inspector to roll the sensing device 200 along the bridge tendon 202 using the wheels 212. A sensor display 210 having a processor and coupled to a sensor 218 is proximate a first end of the sensing device 200 and a battery pack 214 is proximate to a second end of the sensing device 200. In addition, the sensing device 200 may include a location device 215 to determine the location of the sensing device 200 on the bridge tendon 202.

Figure 7:
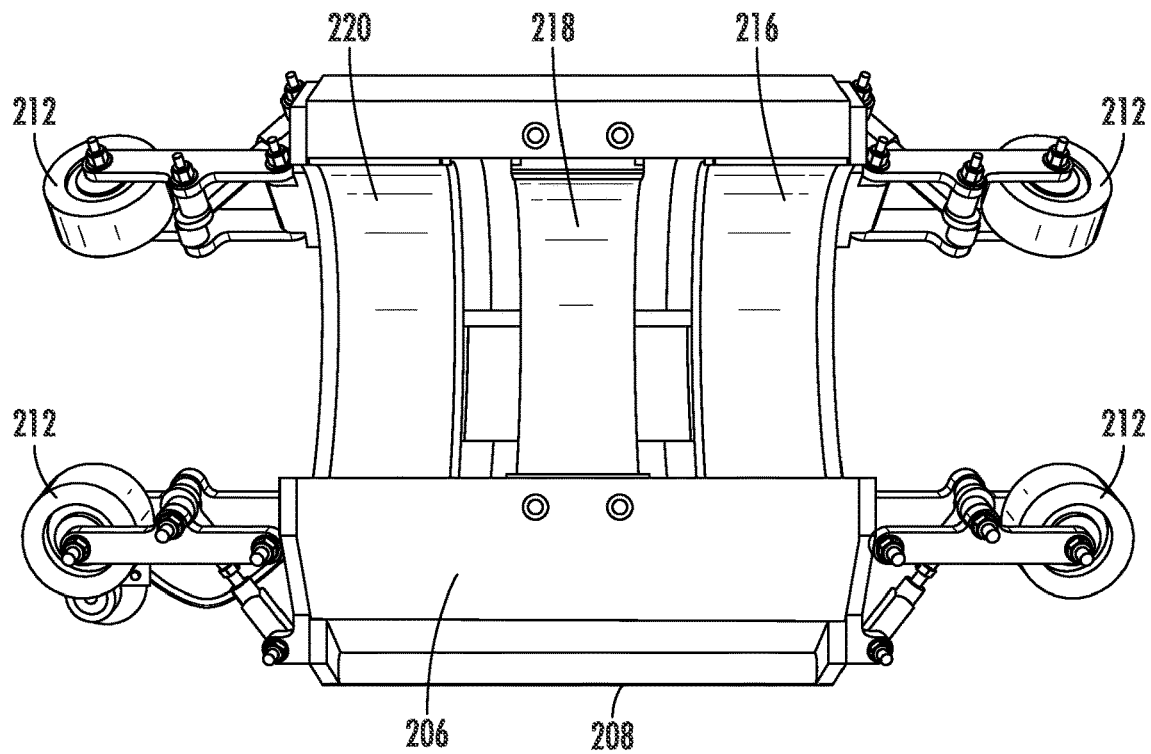
FIG. 7 is an elevational side view of an open side of the sensing device.
Figure 8:
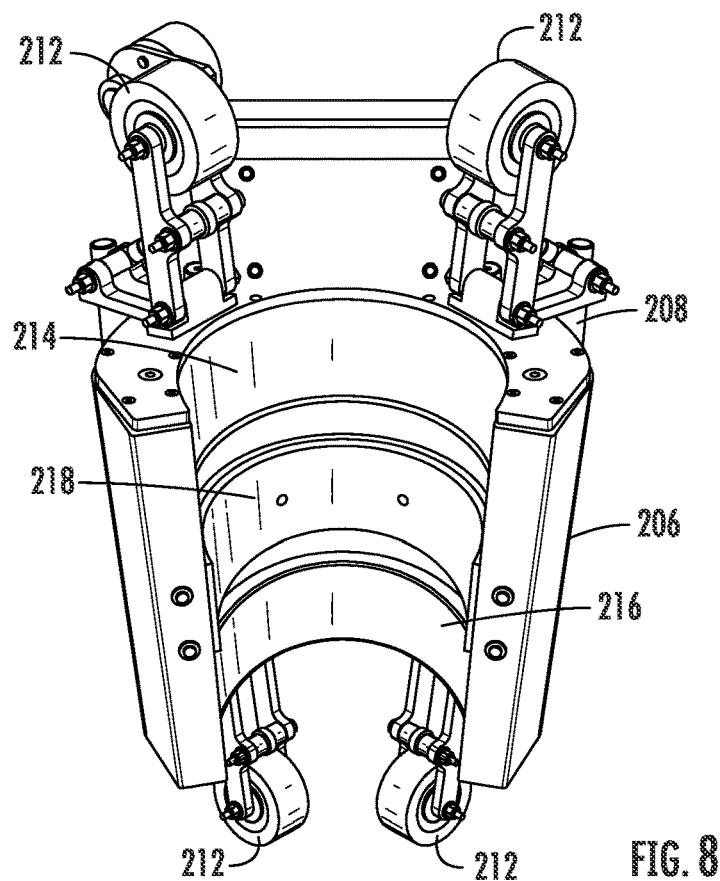
FIG. 8 is a top perspective view of the sensing device.

In particular, the sensing device 200 comprises an annulus sector shape of 240 degrees and having a 120 degree opening as shown in FIGS. 7 and 8. In other aspects of the sensing device 200, the annulus sector shape can vary to be anywhere between about 180 degrees to about 300 degrees.

This is an important feature of sensing device 200 in that a significant amount of bridge tendons 202 are about one inch off the floor (bottom slab) or against the wall (box web) and cannot be inspected by a sensing device that completely surrounds the bridge tendon 202.

The sensing device 200 includes a first magnet 216 that has a curved or arcuate shape and having a first polarity, and a second magnet 220 that has a curved or arcuate shape and having a second polarity which are configured to generate a magnetic field. The magnetic field is sufficient to penetrate substantially through the cross section of the bridge tendon 202 so that all of the cables contained therein are evaluated. The sensing device 200 performs similar to the sensing device 100 of the first embodiment with the sensor 218 detecting magnetic flux leakage but with the annular sector shape allows the sensing device 200 to access tight places where the 360 degree sensing device 100 cannot.

Referring now to FIG. 9, results of a non-destructive evaluation of external post-tensioned tendons of segmental bridges can be generated in a graph 300 to make it easy to interpret by the inspector. The results are included as part of a bridge tendon condition assessment report that is generated using the inspection results from the sensing device 200 and identifies locations and sizes of these discontinuities. By accurately detecting deficient areas within the external post-tensioned tendons of segmental bridges, repairs can be made more quickly and can be more efficiently conducted.

For example, the results of measurements from the sensor 218 that has a curved or arcuate shape as shown in FIGS. 7 and 8 (e.g. raw voltage measurements) are plotted along a measurement line 302 and where magnetic flux leakage is detected is shown in portion 304 of the graph 300. A correlating chart reflects loss of magnetic area (LMA) values 306. As can be seen in FIG. 9, portion 308 of the graph 300 indicates a relative loss of magnetic area that should be flagged for further inspection and/or repair.

Existing inspection methods include drilling random holes in the bridge tendon and looking inside for corrosion. The present robotic inspection system is designed to overcome the shortcomings of the current techniques and methodologies in the art and assist in the preservation of service life of existing bridges. In particular, the robotic inspection system is configured to pinpoint discontinuities within a bridge tendon, which may indicate need for a repair and helps to manage bridge tendon maintenance over time.

In operation, the inspector stands at a control station located on a wheeled cart and moves along with the sensing device. The sensing device 200 may use wireless connectivity to transmit the data to the control station where the inspector performs real-time assessments of the discontinuities within the bridge tendon.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A robotic inspection system to detect discontinuities within external post-tension bridge tendons, the system comprising:

a sensing device having a first arcuate magnet of a first polarity and a longitudinally spaced apart second arcuate magnet of an opposing second polarity, the sensing device configured to move along an outer surface of a bridge tendon to detect magnetic flux leakage within the bridge tendon;

a location device coupled to the sensing device configured to determine the location of the sensing device on the bridge tendon; and a control station configured to wirelessly interface with the sensing device and the location device, the control station configured to generate a bridge tendon condition assessment report from the detection of the magnetic flux leakage to identify locations and sizes of the discontinuities within the bridge tendon;

wherein the first and second arcuate magnets comprise an annulus sector shape of about 240 degrees.

2. The robotic inspection system of claim 1, wherein the sensing device comprises a sensor array.

3. The robotic inspection system of claim 2, wherein the sensing device comprises a processor configured to analyze raw voltage measurements.

4. The robotic inspection system of claim 2, wherein the sensing device comprises an annulus sector shape of 240 degrees and having a 120 degree opening.

5. The robotic inspection system of claim 2, wherein the sensor array comprises an inductive coil sensor configured to detect the magnetic flux leakage to indicate a discontinuity within the bridge tendon.

6. The robotic inspection system of claim 2, wherein the sensor array comprises a Hall effect sensor configured to detect the magnetic flux leakage to indicate a discontinuity within the bridge tendon.

7. The robotic inspection system of claim 2, wherein the first and second magnets are configured to magnetize the bridge tendon along a longitudinal direction.

8. The robotic inspection device of claim 2, wherein the sensor array is configured to detect the magnetic flux leakage perpendicular to a surface of the bridge tendon.

9. The robotic inspection system of claim 2, wherein the sensing device comprises an annulus shape configured to open to be secured completely around the bridge tendon.

10. A robotic inspection system to detect discontinuities within external post-tension bridge tendons, the system comprising:

a sensing device configured to move along a bridge tendon to detect magnetic flux leakage within the bridge tendon;

an arcuate sensor array coupled to the sensing device and having an inductive coil sensor or Hall effect sensor configured to detect the magnetic flux leakage to indicate a discontinuity within the bridge tendon;

a plurality of magnets coupled to the sensing device to magnetize the bridge tendon, wherein the plurality of magnets comprise a first arcuate magnet of a first polarity and a longitudinally spaced apart second arcuate magnet of an opposing second polarity, and the first and second arcuate magnets having an annulus sector shape of about 240 degrees; and a processor coupled to the arcuate sensor array and configured to analyze raw voltage measurements.

11. The robotic inspection system of claim 10, wherein the sensing device comprises an annulus sector shape of 240 degrees and having a 120 degree opening.

12. The robotic inspection system of claim 10, wherein the magnets are configured to magnetize the bridge tendon along a longitudinal direction.

13. The robotic inspection device of claim 10, wherein the arcuate sensor array is configured to detect the magnetic flux leakage perpendicular to a surface of the bridge tendon.

14. The robotic inspection system of claim 10, wherein the sensing device comprises an annulus shape configured to open to be secured completely around the bridge tendon.

* * * * *